US012558312B2

(12) United States Patent
Wang

(10) Patent No.: US 12,558,312 B2
(45) Date of Patent: Feb. 24, 2026

(54) SOLID DOSAGE FORM FOR TRANSMUCOSAL DRUG DELIVERY

(71) Applicant: Primo Pharmatech LLC, Somerset, NJ (US)

(72) Inventor: Zheng Wang, Bridgewater, NJ (US)

(73) Assignee: PRIMO PHARMATECH LLC, Somerset, NJ (US)

( * ) Notice: Subject to any disclaimer, the term of this patent is extended or adjusted under 35 U.S.C. 154(b) by 595 days.

(21) Appl. No.: 18/055,239

(22) Filed: Nov. 14, 2022

(65) Prior Publication Data

US 2023/0121000 A1 Apr. 20, 2023

Related U.S. Application Data

(63) Continuation-in-part of application No. PCT/US2021/032448, filed on May 14, 2021.

(60) Provisional application No. 63/024,908, filed on May 14, 2020.

(51) Int. Cl.

| | |
|---|---|
| ***A61K 31/519*** | (2006.01) |
| ***A61K 9/00*** | (2006.01) |
| ***A61K 31/00*** | (2006.01) |
| ***A61K 31/05*** | (2006.01) |
| ***A61K 31/522*** | (2006.01) |
| ***A61K 31/706*** | (2006.01) |
| ***A61K 31/728*** | (2006.01) |
| ***A61K 38/095*** | (2019.01) |
| ***A61K 47/10*** | (2017.01) |
| ***A61K 47/12*** | (2006.01) |
| ***A61K 47/26*** | (2006.01) |

(52) U.S. Cl.

CPC .............. *A61K 9/006* (2013.01); *A61K 31/05* (2013.01); *A61K 31/522* (2013.01); *A61K 31/658* (2023.05); *A61K 31/706* (2013.01); *A61K 31/728* (2013.01); *A61K 38/095* (2019.01); *A61K 47/10* (2013.01); *A61K 47/12* (2013.01); *A61K 47/26* (2013.01)

(58) Field of Classification Search

None

See application file for complete search history.

(56) References Cited

U.S. PATENT DOCUMENTS

| | | | | |
|---|---|---|---|---|
| 2004/0224039 A1* | 11/2004 | Brucker | A61K 36/71 514/47 |
| 2012/0000399 A1 | 1/2012 | Aden et al. | |
| 2019/0085008 A1 | 3/2019 | Kluge et al. | |
| 2019/0224223 A1 | 7/2019 | Imai et al. | |
| 2019/0328758 A1 | 10/2019 | Alvarez et al. | |

FOREIGN PATENT DOCUMENTS

WO WO-2020243538 A1 * 12/2020 ......... A61K 31/4045

* cited by examiner

*Primary Examiner* — Brian Gulledge

(74) *Attorney, Agent, or Firm* — FOX ROTHSCHILD LLP

(57) ABSTRACT

A solid dosage form for oral transmucosal delivery of an active pharmaceutical ingredient (API) is disclosed. Also provided are methods of treating a disease with the solid dosage form.

20 Claims, No Drawings

SOLID DOSAGE FORM FOR TRANSMUCOSAL DRUG DELIVERY

TECHNICAL FIELD

The patent document relates to a delivery system which provides improved delivery of therapeutic agents. In particular, the present invention relates to buccal and sublingual formulations.

BACKGROUND

The effective delivery of therapeutic agents is often dependent on various factors including the efficiency of drug uptake, drug loading in a dosage form, potential side effect, and patient compliance. For instance, conventional oral administration of a therapeutic agent can lead to unwanted gastrointestinal side effect. For certain pediatric and adult patient populations, the ability to swallow solid dosage medicament formulations can be hampered by disease conditions. As a result, patient compliance becomes a serious hurdle for effective treatment. Further, for those agents that require a high loading to achieve a desirable therapeutic effect, there often lacks a suitable dosage form that can provide a target dose with minimized side effects.

Accordingly, there is a need to deliver therapeutic agents to a patient in a convenient and effective manner. In particular, a desirable dosage form would promote patient compliance without comprising the efficacy of the agents.

SUMMARY

An aspect of this patent document provides a solid dosage form for oral transmucosal delivery of of an active pharmaceutical ingredient (API). The dosage form includes a therapeutically effective amount of API for oral transmucosal delivery; a water-soluble polymer, a surfactant; and optionally a fatty acid, wherein the surfactant and the fatty acid if present are so combined that their HLB value ranges from about 6 to about 15.

Another aspect provides a method of delivering an API transmucosally to a subject. The method includes administering to the subject the dosage form disclosed herein. Preferably, the water soluble polymer, the surfactant, the softener, the fatty acid, and their respective amounts in the dosage form are selected so that at least 5% of the API in the dosage form is uptaken via oral transmucosal delivery.

Another aspect provides a method of preparing the dosage form for oral transmucosal delivery of an API. The method includes mixing an API, a water-soluble polymer, a surfactant and a fatty acid, wherein the surfactant and the fatty acid are so combined that their HLB value ranges from about 6 to about 15.

Another aspect provides a method of treating a disease or condition in a subject. The method includes administering to the subject a dosage form described herein.

DETAILED DESCRIPTION

Various embodiments of this patent document provide a solid dosage form for oral mucosae delivery of a pharmaceutically active ingredient (API) or a therapeutical agent. It has been discovered that by combining a fatty acid and a surfactant, the resulting dosage form provides an effective buccal and/or sublingual delivery of the intended agent. Meanwhile, the dosage form can be conveniently administered to a subject in need and minimize non-compliance issues. Further, various agents can be formulated into a dosage form with methods described herein and have extended shelf life.

The API is formulated for fast uptake through sublingual, buccal and gingiva delivery. Furthermore, the convenience with which the dosage form can be self-administered provides a significant advantage to severely patients with compromised motor skills.

While the following text may reference or exemplify specific embodiments of a dosage form or a method of treating a disease or condition, it is not intended to limit the scope of the dosage form or method to such particular reference or examples. Various modifications may be made by those skilled in the art, in view of practical and economic considerations, such as the excipient of the formulation and the amount or administration of the API for treating a disease or condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "active pharmaceutical ingredient" (API) as used herein refers to a compound or an agent that provides a therapeutic effect for treating a disease or a condition in a subject.

The term "carrier" or "excipient" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "film" as used herein includes thin films, sheets and wafers, in any shape, including rectangular, square, or other desired shape. The films described herein may be any desired thickness and size such that it may be placed into the oral cavity of the user. For example, the films may have a relatively thin thickness of from about 0.1 to about 10 millimeters, or they may have a somewhat thicker thickness of from about 10 to about 30 millimeters. For some films, the thickness may be even larger, i.e., greater than about 30 millimeters. Films may be in a single layer or they may be multi-layered, including laminated films.

The term "physiologically acceptable" or "pharmaceutically acceptable" refers to a carrier or diluent that does not abrogate the biological activity and properties of the compound.

The term "subject" refers to as a human or an animal.

The term "effective amount" or "therapeutically effective amount" refers to an amount of a compound effective to inhibit bacterial growth, or prevent, alleviate or ameliorate symptoms of disease or prolong the survival of the subject being treated. Determination of a therapeutically effective amount is well within the capability of those skilled in the art, especially in light of the detailed disclosure provided herein.

The term “oral transmucosal delivery” refers to the uptake or absorption of an API through sublingual mucosa and/or buccal mucosa. Oral mucosa includes sublingual mucosa, buccal mucosa, gingival mucosa, palatal mucosa, and the inside of the lips. However, uptake or absorption through oral mucosa takes place mainly through through sublingual mucosa and/or buccal mucosa. The dosage form disclosed herein can be administered sublingually or via sublingual delivery, which is the administration of the dosage form through the mucosa inside the oral floor and/or below the tongue. The dosage form can also be administered buccally or via buccal delivery, which is the administration of the dosage form through the mucosa inside the cheek. When delivering an API transmucosally or administering a dosage form transmucosally, the dosage form is administered or placed sublingually (on the oral floor and/or below the tongue) and/or buccally (between the inside of the cheek and the teeth and gums).

The term “treating” or “treatment” of any disease or condition refers, in some embodiments, to ameliorating the disease or disorder (i.e., arresting or reducing the development of the disease or at least one of the clinical symptoms thereof). In some embodiments “treating” or “treatment” refers to ameliorating at least one physical parameter, which may not be discernible by the subject. In some embodiments, “treating” or “treatment” refers to modulating the disease or disorder, either physically, (e.g., stabilization of a discernible symptom), physiologically, (e.g., stabilization of a physical parameter), or both. In some embodiments, “treating” or “treatment” refers to delaying the onset of the disease or disorder, or even preventing the same. “Prophylactic treatment” is to be construed as any mode of treatment that is used to prevent progression of the disease or is used for precautionary purpose for persons at risk of developing the condition.

Dosage Form

An aspect of this patent document provides a dosage form formulated for oral transmucosal delivery of an API or a therapeutic agent. The dosage form generally includes an API, a surfactant and optionally a fatty acid. In some embodiments, the surfactant and the fatty acid are so selected that their combined HLB value ranges from about 6 to about 15 in order to ensure desrale permeation of the agent across the mucosea tissue or membrane for buccal and/or sublingual delivery.

The dosage form can be in various form suitable for oral mucosa delivery. Non-limiting examples include a quick dissolve tablet, a film, a powder, an effervescent tablet, a hard gelatin capsule, a soft gelatin capsule, a non-aqueous liquid, an aqueous liquid, a granule, a capsule, a suspension, a solution, an emulsion, a syrup, a sterilized aqueous suspension or solution, a non-aqueous suspension or solution, a lyophilized formulation, or a suppository. In some embodiments, the dosage is in a solid form.

In some embodiments, the dosage is in a solid form. The dosage form may be in any suitable form including for example, an oral dispersible pill, a chewable pill, a buccal adhesive pill, a tablet, a capsule, a granular powder, a troche, a dragée, a buccal adhesive pill, and a film. The dosage form may be multi-layered to optimize disintegration of the formulation, and/or dispersion of the API or medicament, in the vehicle. In some embodiments, the dosage includes a water soluble polymer, which can be used for example as a plasticizer, or shape forming agent. Non-limiting examples of the polymer include polyvinylpyrrolidone (PVP), pullulan (PU), (hydroxypropyl methylcellulose (HPMC), polyethyl oxide (PEO), polyvinyl alcohol (PVA), sodium carboxymethyl cellulose (CMC-Na), sodium alginate, Konjac gum, xanthan gum, carigena, polyacrylates, polymethacrylates and copolymers and any combination thereof. In some embodiments, the water soluble polymer ranges from about 1% to about 70%, from about 1% to about 60%, from about 1% to about 35%, from about 1% to about 25%, from about 5% to about 20%, from about 5% to about 15% by weight. In some embodiments, the polymer is less than 5%, less than 10%, less than 15%, less than 20%, less than 30%, less than 40%, less than 50% or less than 60% in the dosage form by weight. Nonlimiting examples of the polymer include about 1%, about 5%, about 10%, about 15%, about 20%, about 25%, about 30%, about 40%, and about 50% by weight in the dosage form.

Various agents, alone or in combination, can be formulated as API according to the dosage form and methods described herein. Non-limiting examples of the agent in the formulation include Nicotinamide mononucleotide (NMN), caffeine, curcumine, proanthocyanidins (PAC), Astaxanthin, Resveratrol, melatonin, cysteine, vitamin C, biotin, small peptides._or active pharmaceutical ingredients, and any combination thereof. In some embodiments, the API comprises a monomer selected from the group consisting of NMN, cannabidiol (CBD), oxytocin, difelikefalin, octreotide, sildenafil citrate, hyaluronic acid, thymopentin, caffeine, curcumine, proanthocyanidins (PAC), astaxanthin, resveratrol, allicin, melatonin, cysteine, vitamin C, biotin, probiotic blends, and any combination thereof. In some embodiments, the API is selected from the group consisting of NMN, caffeine, curcumine, proanthocyanidins (PAC), astaxanthin, resveratrol, allicin, melatonin, cysteine, vitamin C, biotin, probiotic blends, and any combination thereof. In some embodiments, the agent consists essentially of NMN. In some embodiments, the agent includes NMN and one or more additional therapeutic components. In some embodiments, the agent includes CBD. In some embodiments, the agent includes a small peptide having a molecular weight of 1200 Da or less (e.g. about 1200, about 1100, about 1000, about 900, about 800, about 700, about 600, about 500 or about 400 or any ranges between the above values).

The mixture of the surfactant and the optional fatty acid serves as the permeation enhancer of the API or active agent. Depending on factoring including for example the specific agent to be formulated and the intended use, the individual amount of the surfactant and the fatty acid may be adjusted. In some embodiments, the HLB value of the combination of the surfactant and the fatty acid ranges from about from about 6.5 to about 14.5, from about 7 to about 14, from about 7.5 to about 13.5, from about 8 to about 13, from about 8.5 to about 13, from about 8.5 to about 12.5, from about 9 to about 12, from about 10 to about 12, from about 8 to about 12 or from about 8 to about 15. In further exemplified embodiments, the HLB value of the surfactant and the fatty acid in combination is about 7, about 8, about 8.5, about 9, about 9.5, about 10, about 11, about 12, about 13, about 14, about 15, or any range between any two of these values.

The fatty acid serves to facilitate the permeation of the agent through the oral mucosae for effective delivery. Non-limiting examples of the fatty acid includes caprylic acid, capric acid, lauric acid, myristic acid, palmitic acid, stearic acid, oleic acid, ricinoleic acid, linolenic acid, eicosenoic acid, behenic acid, and erucic acid. One or more additional permeation enhancers can be used if necessary. In some embodiments, the fatty acid is oleic acid.

The amount of the fatty acid can range from about 0.1% to about 15% or from about 0.2% to about 8% in the solid dosage form. In exemplary embodiments, the fatty acid ranges from about 0.25% to about 7%, from about 0.25% to about 6%, from about 0.25% to about 5%, from about 0.25% to about 4%, from about 0.25% to about 3%, from about 0.25% to about 2%, from about 0.25% to about 1%, from about 0.4% to about 7%, from about 0.4% to about 6%, from about 0.4% to about 5%, from about 0.8% to about 7%, from about 0.8% to about 6%, from about 0.8% to about 5%, from about 1% to about 5%, from about 1% to about 3%, or from about 2% to about 4%. Further exemplary embodiments of the amount of the fatty acid in the dosage form include about 0.15%, about 0.20%, about 0.25%, about 0.4%, about 0.6%, about 0.8%, about 1%, about 1.5%, about 2%, about 2.5%, about 3%, about 3.5%, about 4%, about 4.5%, about 5%, about 6%, about 7%, or about 8% by weight.

The surfactant contributes to the physical appearance and stability of the dosage form. In addition, when mixed with the fatty acid, it helps with the adjustment of the HLB value and absorption and permeation of the agent. Exemplary embodiments of the surfactant include PEG-fatty acid esters include those with a molecular weight up to 8000 and the fatty acid component can be selected from any suitable fatty acid such as laurate, dilaurate, oieate, stearate, glycerol trioleate, dioleate, glyceryl laurate, glyceryl oieate, palm kernel oil, hydrogenated castor oil, caster oil, corn oil, caprate/captylate glycerides, polyglyceryl-10 laurate, phytosterols, cholesterol, soya sterol, sorbitan oieate and sorbitan laurate. Other examples of suitable PEGs include polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, polyglyceryl-10 oieate, Tween 40, Tween 60, sucrose monostearate, sucrose monolaurate, sucrose monopalmitate, PEG 10-100 nonyi phenol series, PEG 15-100 octyl phenol series, a poloxamer, and mixtures thereof. The PEG can be selected to alter pharmacokinetics of the buccal matrix in a way to achieve either a zero or first order release rate depending upon the administration of the API.

In some embodiments, the surfactant contains a PEG moiety and a fatty acid moiety. The selection of the PEG or PEG derivative and the amount used will depend on the active compound(s) to be included in the formulation. A person skilled in the art will be able to select a suitable PEG or PEG derivative to achieve the predetermined pharmacokinetics for a particular active ingredient because the properties of PEGs are well known. In particular, it has been known for some time that a low molecular weight PEG is usually a liquid whereas a higher molecular weight PEG tends to be a waxy solid. It is also known that PEGs can complex with other compounds. Examples of such complexation include pegylation and PEG-fatty acid esters. These PEG complexes have different properties to the PEG alone which are useful when used in the present invention. For example, some pure uncomplexed PEGs having a molecular weight below 2000 floculate or exist as a liquid gel at room temperature which can make it difficult to use in a dry powder tabletting process, in contrast, the complexes of these low molecular weight PEGs are able to be used in a dry powder tabletting process. A person skilled in the art will know the properties of the different PEGs and PEG derivatives and be able to select the appropriate one to use with the selected active ingredient to provide the predetermined pharmacokinetics. Besides PEG, chitosan and hyaluronic acid can also be used to provide similar results.

In some embodiments, the surfactant is a polysorbate which is derived from ethoxylated sorbitan (a derivative of sorbitol) esterified with fatty acids. In the nomenclature of polysorbates, the numeric designation following polysorbate refers to the lipophilic group. Examples of polysorbates include Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate), and Polysorbate 80 (polyoxyethylene (20) sorbitan monooleate, CAS #9005-65-6). Additional examples of surfactant include polyoxyethylene lauryl ether, polyoxyethylene monostearate, triethanolamine oleate, polyoxyethylene alkyl phenol, polyethylene glycol 400 monolaurate, and polyoxyethylene lauryl ether.

In some embodiments, the permeation enhancer of the dosage form includes a fatty acid and a surfactant. In some embodiments, the permeation enhancer consists essentially of a fatty acid and a surfactant. In some embodiments, the permeation enhancer consists essentially of oleic acid and polysorbate 80. The phrase "consisting essentially of" indicate that any additional component will not change the overall HLB value of the permeation enhancer. In some embodiments, the permeation enhancer consists essentially of oleic acid and polysorbate 80, which is often represented as the formula below.

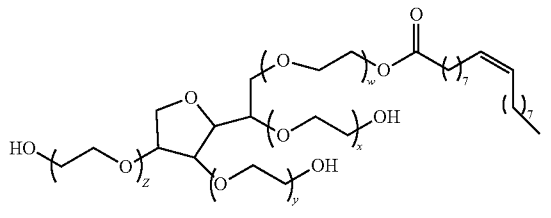

w+x+y+z=20 polysorbate 80

The amount of the surfactant in the dosage form depends on the agent to be formulated, the intended use, and other excipients such as the fatty acid. In exemplary embodiments, the surfactant ranges from about 0.25% to about 15%, from about 0.25% to about 10%, from about 0.25% to about 8%, from about 0.25% to about 5%, from about 0.25% to about 3%, from about 0.5% to about 10%, from about 0.5% to about 8%, from about 0.5% to about 5%, from about 0.5% to about 3%, from about 0.5% to about 1%, from about 1% to about 10%, from about 2% to about 5%, from about 2% to about 6%, from about 2% to about 7%, from about 2% to about 8%, from about 2% to about 4%, from about 1% to about 4% or from about 1% to about 3%. Further exemplary embodiments of the amount of the surfactant in the dosage form include about 0.25%, about 0.4%, about 0.6%, about 0.8%, about 1%, about 1.5%, about 2%, about 2.5%, about 3%, about 3.5%, about 4%, about 4.5%, about 5%, about 6%, about 6.5%, about 7%, about 8% and about 10% by weight.

The amount and ratio of the fatty acid and the surfactant impact the absorption and permeation of the therapeutic agent and physical appearance of the dosage form. As illustrated in the examples below, too high or too low percentage of the surfactant may change the HLB value or physical properties. For instance, a high amount of surfactant may drive the HLB outside a desirable range and excessively soften the dosage form. Insufficient surfactant, on the other hand, will also decrease the flexibility and uniformity of the dosage form. Likewise, it is important to keep the fatty acid in a suitable range to control the lipophilicity of the dosage form and maintain a desirable HLB so that the permeation of the active agent or ingredient through oral mucosae can take place smoothly.

In some embodiments, the ratio between the fatty acid and the surfactant ranges from about 2:1 to about 1:100, from about 1:1 to about 1:50, from 2:3 to about 1:100, from about 1:15 to about 2:1, from about 1:13 to about 11:9, from about 1:10 to about 2:1, from about 1:8 to about 1:1, from about 1:6 to about 1:1, from about 1:6 to about 1:1, from about 1:4 to about 1:1, or from about 1:4 to about 1:2 by weight. Non-limiting examples of the ratio between the fatty acid and the surfactant include 2:1, 1:1, 2:3, 1:2, 2:5, 1:3, 1:4, 1;5, 1:6, 1:8, 1:10, 1:12, 1:15, 1:20, 1:25, 1:30, 1:35, 1:40, 1:50: 1:60, 1:70, 1:80, 1:100, or any range between any two of these ratios. In some embodiments, the dosage form is substantially free from the surfactant. In some embodiments, the dosage form is substantially free from the fatty acid. In some embodiments, the surfactant is polysorbate 80. In some embodiments, the fatty acid is oleic acid.

In the combination of the fatty acid and the surfactant, the fatty acid may range from about 10% to about 55%, from about 10% to about 50%, from about 20% to about 50%, from about 20% to about 40%, from about 20% to about 35%, or from about 25% to about 30%. In exemplary embodiments, the fatty acid is about 10%, about 15%, about 20%, about 25%, about 30%, about 35%, about 40%, about 45%, about 50%, or about 55% by weight in the combination of the fatty acid and the surfactant. The percentage of the surfactant in the combination can be calculated accordingly.

The total amount of the fatty acid and the surfactant also impacts the permeation efficiency of the agent as well as the physical appearance and stability of the dosage form. In some embodiments, the combination of the fatty acid and the surfactant is about 1%, about 2%, about 3%, about 4%, about 5%, about 6%, about 8%, about 10%, about 12%, about 14%, about 16%, or about 20% by weight in the solid dosage form.

The dosage form disclosed herein enables high loading of agents for oral mucosa delivery. In some embodiments, the API or therapeutic agent is more than 5%, more than 10%, more than 15%, more than 20%, more than 30%, more than 40%, more than 50%, more than 60%, more than 70% or more than 80% by weight in the dosage form. In some embodiments, the dosage form contains at least 5%, at least 10%, at least 15%, at least 20%, at least 25%, at least 30%, at least 40%, at least 50%, at least 60%, at least 70%, or at least 80% of the therapeutic agent (e.g. NMN) by weight in the dosage form, and optionally one or more additional agents such as caffeine, curcumine, proanthocyanidins (PAC), Astaxanthin, Resveratrol, melatonin, cysteine, vitamin C, biotin, small peptides, any active pharmaceutical ingredients, and any combination thereof.

In some embodiments, the dosage form (as a physically distinct unit form) comprises, consists essentially of, or consist of the therapeutic agent (e.g. NMN or other agents disclosed herein), a salt thereof and/or a prodrug thereof in an amount of about 100 mg, from 25 mg to 2000 mg, about 2000 mg, or greater. In some embodiments, the dosage form can comprise, consist essentially of, or consist of NMN, a salt thereof and/or a prodrug thereof in an amount of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, or greater. In some embodiments, the dosage form can comprise, consist essentially of, or consist of NMN, a salt thereof and/or a prodrug thereof in an amount of 50-150 mg, 151-250 mg, 251-350 mg, 351-450 mg, 451-550 mg, 561-650 mg, 651-750 mg, 751-860 mg. 861-950 mg, 951-1050 mg, 1051-1150 mg, 1151-1250 mg, 1251-1350 mg, 1351-1450 mg, 1451-1550 mg, 1551-1650 mg, 1651-1750 mg, 1751-1850 mg, 1851-1950 mg, 1951-2000 mg, or greater. In some embodiments, the dosage form can comprise, consist essentially of, or consist of NMN, a salt thereof and/or a prodrug thereof in an amount of at least 0.5 mg up to about 6800 mg, such as, without limitation, 0.5 mg, about 0.5 mg, 1 mg, about 1 mg, 5 mg, about 5 mg, 10 mg, about 10 mg, 20 mg, about 20 mg, 30 mg, about 30 mg, 40 mg, about 40 mg, 50 mg, about 50 mg, 60 mg, about 60 mg, 70 mg, about 70 mg, 80 mg, about 80 mg, 90 mg, about 90 mg, 100 mg, about 100 mg, 150 mg, about 150 mg, 200 mg, about 200 mg, 250 mg, about 250 mg, 300 mg, about 300 mg, 400 mg, about 400 mg, 450 mg, about 450 mg, 500 mg, about 500 mg, 600 mg, about 600 mg, 680 mg, about 680 mg, 700 mg, about 700 mg, 800 mg, about 800 mg, 900 mg, about 900 mg, 1000 mg, about 1000 mg, 1100 mg, about 1100 mg, 1130 mg, about 1130 mg, 1200 mg, about 1200 mg, 1300 mg, about 1300 mg, 1350 mg, about 1350 mg, 1360 mg, about 1360 mg, 1400 mg, about 1400 mg, 1500 mg, about 1500 mg, 1600 mg, about 1600 mg, 1700 mg, about 1700 mg, 1800 mg, about 1800 mg, 1900 mg, about 1900 mg, 2000 mg, about 2000 mg, 2040 mg, about 2040 mg, 2100 mg, about 2100 mg, 2200 mg, about 2200 mg, 2250 mg, about 2250 mg, 2300 mg, about 2300 mg, 2400 mg, about 2400 mg, 2500 mg, about 2500 mg, 2600 mg, about 2600 mg, 2700 mg, about 2700 mg, 2800 mg, about 2800 mg, 2900 mg, about 2900 mg, 3000 mg, about 3000 mg, 3100 mg, about 3100 mg, 3200 mg, about 3200 mg, 3300 mg, about 3300 mg, 3400 mg, about 3400 mg, 3500 mg, about 3500 mg, 3600 mg, about 3600 mg, 4000 mg, about 4000 mg, 4500 mg, about 4500 mg, 5000 mg, about 5000 mg, 5500 mg, about 5500 mg, 6000 mg, about 6000 mg, 6500 mg, about 6500 mg, 6800 mg, or about 6800 mg.

In some embodiments, the dosage form can contain the therapeutic agent, a pharmaceutical salt thereof, or a prodrug of thereof. The salt can be a pharmaceutically acceptable salt; that is, a salt prepared from pharmaceutically acceptable non-toxic acids, including inorganic acids and organic acids. Non-limiting examples of suitable non-toxic acids include inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N"-dibenzylethylenediamine, chloroprocaine, diethanolamine, procaine, n-benzylphenethylamine, diethylamine, piperazine, tris(hydroxymethyl)-aminomethane, tetramethylammonium hydroxide, and the like. Pharmaceutically acceptable salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts can be found in Remington's Pharmaceutical Sciences, 17th ed., Mack Publishing Company, Easton, Pa., 1985, p. 1418, the disclosure of which is hereby incorporated by reference.

The dosage form also includes other pharmaceutically acceptable carriers and/or excipients such as softeners, stabilizers, binders, lubricants, diluents, coatings, disintegrate, barrier layer components, glidants, colouring agents, solubility enhancers, gelling agents, fillers, proteins, co-factors, emulsifiers, solubilising agents, suspending agents and mixtures thereof.

A coating material or film forming component can be used for the dosage form descried herein. Nonlimiting examples include ethylcellulose, methylcellulose, hydroxypropyl cellulose, hydroxypropylmethyl cellulose, cellulose acetate, cellulose acetate phthalate, polyvinyl alcohol, polyacrylates, polymethacrylates and copolymers thereof. Additional examples include glucose, fructose, mannitol, mannose, galactose, sorbitol, pullulan, dextran, water-soluble hydrophilic polymers, hydroxyalkylcelluloses, carboxyalkylcelluloses, hydroxypropylmethylcellulose, cellulose ethers, acrylic resins, polyvinylpyrrolidone, cross-linked polyvinylpyrrolidone, polyethylene oxide, Carbowaxes, Carbopol, diols, polyols, polyhydric alcohols, polyalkylene glycols, polyethylene glycols, polypropylene glycols or block polymers thereof, polyglycols, poly(a-w)alkylenediols. In some embodiments, with the selection of the combination of the fatty acid and the surfactant, the coating material or film forming component is less than 5%, less than 10%, less than 15%, less than 20%, less than 30%, less than 40%, less than 50%, or less than 60% by weight in the dosage form.

Other agents can also be included in the dosage form as a secondary or additional permeation enhancer. Examples of additional permeation enhancer includes bile salts, such as sodium cholate, sodium glycocholate, sodium glycodeoxycholate, taurodeoxycholate, sodium deoxycholate, sodium lithocholate chenocholate, chenodeoxycholate, ursocholate, ursodeoxy-cholate, hyodeoxycholate, dehydrocholate, glycochenocholate, taurochenocholate, and taurochenodeoxycholate; sodium dodecyl sulfate (SDS), dimethyl sulfoxide (DMSO), N-lauroyl sacrcosine, sorbitan monolaurate, stearyl methacrylate, N-dodecylazacycloheptan-2-one, N-dodecyl-2-pyrrolidinone, N-dodecyl-2-piperidinone, 2-(1-nonyl)-1,3-dioxolane, N-(2-methoxymethyl) dodecylamine, N-dodecylethanolamine, N-dodecyl-N-(2-methoxymethyl)acetamide, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 2-dodecyl-2-oxo-1-pyrrolidineacetic acid, 1-azacylioheptan-2-one-dodecylacetic acid, menthol, propylene glycol, glycerol monostearate, sorbitol monolaurate, glycerol dilaurate, tocopherol acetate, phosphatidyl choline, glycerol, polyethyleneglycol, lecithin, tween surfactants, sorbitan surfactants, sodium lauryl sulfate; salts and other derivatives of saturated and unsaturated fatty acids, surfactants, bile salt analogs, derivatives of bile salts, or such synthetic permeation enhancers as described in U.S. Pat. No. 4,746,508, which is incorporated herein by reference. In some embodiments, the additional enhancer can be a PEG derived di-ester, a glycerol-derived mono-ester (e.g. 1-monoacylglycerol), a glycerol-derived di-ester (e.g. 1,2-diacylglycerol, 1,3-diacylglycerol), and a glycerol-derived tri-ester (e.g. triacylglycerol) of a fatty acid. Examples of the fatty acid includes caprylic acid, capric acid, lauric acid, myristic acid, palmitic acid, stearic acid, oleic acid, ricinoleic acid, linolenic acid, eicosenoic acid, behenic acid, and erucic acid.

Softeners soften the dosage form and make the dosage form flexible and/or prevent dryness. Non-limiting examples of softeners include natural oils such as almond oil, coconut oil, olive oil, palm oil, peanut oil and the like. Additional examples of softeners are caprylic/capric triglyceride, castor oil, cetearate-20, cetearate-30, cetearyl alcohol, cetet-20, cetostearyl alcohol, cetyl alcohol, cetyl stearyl alcohol, cocoa butanol, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffin, linoleic acid, mineral oil, white petrolatum, polyethylene glycol, polyoxyethylene glycol fatty alcohol ethers, silicones and mixtures thereof. In some embodiments, the softener include glycerin, propylene glycol, butylene glycol and polyethylene glycol (PEG), and any combination thereof. The PEG may have a molecular weight ranging from about 100 to about 2000, including for example 200, 400, 600, 800, 1000, 1500 daltons. In some embodiments, the dosage form disclosed herein contain a softener ranging from about 1% to about 50% by weight in the dosage form. Nonlimiting examples of the amount of the softener include about 2%, about 5%, about 10%, about 15%, about 20%, about 30%, and about 40%.

In some embodiments, the dosage form disclosed herein contains a stabilizer ranging from about 0.1% to about 10% by weight in the dosage form. Nonlimiting examples of the amount of the stabilizer include about 0.2%, about 0.5%, about 1%, about 2%, about 5%, and about 10%. In some embodiments, the stabilizer ethylenediaminetetraacetic acid (EDTA).

Examples of binders which can be used include acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like. Binders may be used in an amount up to about 60% by weight and advantageously from about 10% to about 40% by weight of the dosage form.

Non-effervescent disintegrants include starches as corn starch, potato starch and modified starches thereof, sweeteners, clays, such as bentonite, micro-crystalline cellulose, alginates, gums such as agar, guar, locust bean, karaya, pectin and tragacanth. Disintegrants may comprise up to about 20% by weight and advantageously between about 2% and about 10% by weight of the final dosage form. Notable, these binders and disintegrants may already be sufficiently present in other components of the dosage form, such as in the gas-producing solid matrix.

Coloring agents may include titanium dioxide, and dyes suitable for food such as those known as F. D. & C. dyes and natural coloring agents such as grape skin extract, beet red powder, beta-carotene, annato, carmine, turmeric, paprika, etc. The amount of coloring used may range from about 0.1% to about 3.5% by weight of the dosage form.

Flavors incorporated in the unit dosage form may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple pear, peach, strawberry, raspberry, cherry, plum, pineapple, apricot and so forth. Flavors, which have been found to be particularly useful, include commercially available orange, grape, cherry and bubble gum flavors and mixtures thereof. The amount of flavoring may depend on a number of factors, including the organoleptic effect desired. Flavors may be present in an amount ranging from about 0.5% to about 3.0% by weight of the unit dosage form. Commonly accepted flavors include grape and cherry flavors, and citrus flavors such as orange. It is also appreciated that inclusion of flavoring agents can also influence the final flavor of the vehicle, furthering compliance with ingestion of the API or therapeutic agent.

A bioadhesive, such as a bioadhesive polymer, may be included in the dosage form to increase the contact time between the dosage form and the oral mucosa, particularly where the dosage form is administered directly into the oral cavity and the vehicle is saliva. Non-limiting examples of known bioadhesives, or mucoadhesives, include carbopol (various grades), sodium carboxy methylcellulose, methylcellulose, polycarbophil (Noveon AA-1), hydroxypropyl methylcellulose, hydroxypropyl cellulose, sodium alginate, and sodium hyaluronate.

Extrinsic or intrinsic lubricants may be incorporated in the material to be tableted. A lubricant which is directly applied to the tableting tool surface in the form of a film, as by spraying onto the die cavity and/or punch surfaces, is known as an extrinsic lubricant. Although extrinsic lubricants can provide effective lubrication, their use requires complex application equipment and methods which add cost and reduce productivity. Magnesium, calcium and zinc salts of stearic acid have long been regarded as the most efficient intrinsic lubricants in common use. Concentrations of 1% or less by weight are usually effective.

Flavouring agents include sweeteners and flavours. Examples of suitable sweeteners and flavours include mannitol, sorbitol, maltitol, lactitol, isomaltitol, erythritol, xylitol, sucrose, ammonium glycyrrhizinate, mango aroma, black cherry aroma, sodium citrate, colloidal silicium dioxide, sucralose; zinc gluconate; ethyl maltitol; glycine; acesulfame-K; aspartame; saccharin; acesulfam K, neohesperidin DC, thaumatin, stevioside, fructose; xylitol; honey; honey extracts; corn syrup, golden syrup, misri, spray dried licorice root; glycerrhizine; dextrose; sodium gluconate; stevia powder; glueono delta-lactone; ethyl vanillin; vanillin; normal and high-potency sweeteners or syrups or salts thereof and mixtures thereof. Other examples of appropriate flavouring agents include coffee extract, mint; lamiacea extracts; citrus extracts; almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; grapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glyceryl tricaproate; glyceryl tricaprylate; glyceryl trieaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides; linoieic glycerides; caprylic/capric glycerides; modified triglycerides; fractionated triglycerides; safrole, citric acid, d-limonene, malic acid and phosphoric acid or salts and/or mixtures thereof.

Taste masking agents are also known as taste receptor blockers, compounds which mask the chalkiness, grittiness, dryness and/or astringent taste properties of an active compound, compounds which reduce throat catch as well as compounds which add a flavour. Examples include taste receptor blockers include Kyron T-134, a glycoprotein extract called miraculin from the fruit of the plant synsepalum dulcificum, ethyl cellulose, hydroxypropyl methylcellulose, arginine, sodium carbonate, sodium bicarbonate, gustducin blockers and mixtures thereof. Additional examples include compounds which mask the chalkiness, grittiness, dryness and/or astringent taste properties of an active compound include those of a natural or synthetic fatty type or other flavorant such as cocoa, chocolate (especially mint chocolate), cocoa butter, milk fractions, vanillin butter fat, egg or egg white, peppermint oil, wintergreen oil, spearmint oil and similar oils. Further examples include compounds which reduce throat catch include combinations of high and low solubility acids. For example high solubility acids suitable for use here Include amino acids (eg alanine, arginine etc), glutaric, ascorbic, malic, oxalic, tartaric, malonic, acetic, citric acids and mixtures thereof. Low solubility acids suitable for use include stearic and aspartic acids plus certain amino acids such as glutamic acid, glutamine, histidine, isoleucine, leucine, methionine, phenylalanine, serine, tryptophan, tyrosine, valine and fumaric acid. Actual amounts used will vary depending on the amount of throat catch or burn exhibited by the active used but will generally be in the range of 1-40%.

Suspending agents to improve texture and consistency include for example xanthan gum, HPMC, Konjac gum, HMW CMC-Na, tetragonolobus, *Acacia glaucophylla, Acacia abyssinica, Acacia nilotica, Acacia gummifera, Acacia arabica*, silica gel, kollldon, eremaphor, kollicoat, solutol, ludipress and mixtures thereof.

In some embodiments, the above components, including one or more of the water soluble polymer, the surfactant, the softener, the fatty acid, and their respective amounts are selected so that at least 3%, at least 4%, at least 5%, at least 6%, at least 7%, at least 8%, at least 9%, at least 10%, at least 11%, at least 12%, at least 15%, at least 18% or at least 20% of the API in the dosage form is uptaken via oral transmucosal delivery. In some embodiments, the dosage form is free from citric acid.

Method of Treatment

Another aspect of this patent document provides a method of treating a disease in a subject, comprising administration of a dosage form described herein in an amount effective to treat the disease. Diseases treatable with the method include neurodegenerative diseases, muscular dystrophy, inflammation disease, metabolic disease, and cardiovascular diseases.

Nonlimiting examples of the diseases include arrhythmia, ischemic heart disease, hypertensive heart disease and pulmonary hypertensive heart disease, valvular disease, and congenital heart disease, Alzheimer's disease, multiple sclerosis, Parkinson's disease, amyotrophic lateral sclerosis, cerebral ischemic disease, Huntington's disease, spinal muscular atrophy, stroke, brain trauma, spinal cord injury, prion disease, diabetic neuropathy, attention deficient disorder, attention deficient hyperactivity disorder (ADHD), adult attention-deficient/hyperactivity disorder (AADD, adult ADHD), learning disorders, neurocognitive disorders, Tic disorders, autism spectrum disorder, Tourette's disorder, schizophrenia, negative symptoms of schizophrenia, cognitive symptoms of schizophrenia, substance/medication-induced psychotic disorder, psychotic disorder due to another medical condition, brief psychotic disorder, schizophreniform disorder, schizoaffective disorder, disruptive mood dysregulation disorder, depression, post-partum depression, persistent depressive disorder (dysthymia), major depressive episode, major depressive disorder, treatment-resistant depression, post-traumatic stress disorder, reactive attachment disorder, disinhibited social engagement disorder, personality disorders (e.g., general personality disorder, paranoid personality disorder, schizoid personality disorder, borderline personality disorder, histrionic personality disorder, narcissistic personality disorder, avoidant personality disorder, dependent personality disorder, obsessive-compulsive personality disorder, antisocial personality disorder, schizotypcal personality disorder), psychopathy, cyclothymic disorder, manic episode, hypomanic episode, bipolar disorder, delusional disorder, obsessive compulsive disorder, hoarding disorder, premenstrual dysphoric disorder, somatic symptom and related disorders (e.g., conversion disorder factitious disorders), intellectual disabilities, communication disorders, motor disorders, catalepsy, catatonia, agitation, hypertension, sleep disorders (e.g., insomnia, sleep apnea, hypersomnolence, narcolepsy, nightmare disorder, sleep-wake disorders, non-rapid eye movement sleep arousal disorders, sleepwalking, sleep terrors, rapid eye movement sleep behavior disorder, substance/medication-induced sleep disorder), sexual dysfunctions (e.g., delayed ejaculation, erectile disorder, female orgasmic disorder, female sexual interest/arousal disorder, genito-pelvic pain/penetration disorder, male-hypoactive sexual desire disorder, premature ejaculation, substance/medication-induced sexual dysfunction), anxiety disorders (e.g., selective mutism, generalized anxiety disorder, panic disorder, panic attack, social anxiety disorder, specific phobias, agoraphobia, separation anxiety, hypochondria, substance/medication induced anxiety disorder), adjustment disorders, body dysmorphic disorder, Trichotillomania, excoriation disorder, substance/medication-induced obsessive-compulsive and related disorder, dementias, neurodegenerative diseases (e.g., mild cognitive impairment, Alzheimer's disease, lewy body dementia, frontotemporal dementia, traumatic brain injury, prion diseases, Huntingtion's disease, Parkinson's disease, chronic traumatic encephalopathy, amyotrophic lateral sclerosis, mixed dementias, vascular dementia, hydrocephalus), seasonal affective disorder, pseudobulbar affect, cluster headache, headaches, migraines, Tension-type headaches, tinnitus, hallucinations, delusions, epilepsies, cyclic vomiting syndrome, cannabinoid hyperemesis, nausea, restless leg syndrome, weight loss or binge eating, anorexia nervosa, bulimia nervosa, alcoholism, nicotine dependence, substance use disorders, non-substance related disorders (e.g., gambling disorder, gaming), oppositional defiant disorder, intermittent explosive disorder, conduct disorder, pyromania, kleptomania, paraphilic disorders, medication induced movement disorders, adverse effects of other medications (e.g., antidepressant discontinuation syndrome, neuroleptic malignant syndrome), autoimmune diseases, acute pain, chronic pain, neuropathic pain, cancer, cough, infections, tinnitus, hearing loss, loss of taste, loss of smell, endocrine diseases and disorders, diabetes, gastrointestinal tract related diseases, urinary tract diseases, blood diseases, cardiovascular disease, inflammatory diseases, arthritis, paralysis, spinal cord injury, coagulation, seizure (focal, or partial seizures; generalized-onset seizures such as absence seizures, myoclonic seizures, tonic and atonic seizures, tonic, clonic and tonic-clonic (formerly called grand mal) seizures), inflammation, weight gain via adipogenesis, anxiety, abnormal cell proliferation, stress, muscle pain (e.g. fibromyalgia), covid-19, long covid, stroke, psychosis, infection with staph a., depression, diabetes mellitus (type 1 and type 2), postpartum bleeding or hemorrhage, acromegaly/carcinoid syndrome, auto-immune and immunodeficiency disorders, and pruritus chronic kidney disease (ckd)-hemodialysis (hd).

Additional examples of diseases or conditions treatable with the methods disclosed herein include hypertension, inflammation, osteoarthritis, rheumatoid arthritis, endothelial dysfunction, dermatological condition, ophthalmological condition, bacterial infection, viral infection, ischemia reperfusion injury, hypoxia reoxygenation injury, cytokine storm phenomena, cerebral malaria, Chagas disease, hemoglobinopathies, type 2 diabetes, Alzheimer's disease, Lupus, cystic fibrosis, acute respiratory distress syndrome, pulmonary fibrosis, chronic obstructive pulmonary disease (COPD), bronchiectasis, pulmonary infections including tubercolosis, and pulmonary hypertension.

In some embodiments, the disease or condition is selected from cytokine storm phenomena caused by an infectious disease, which can be for example Coronaviruses, Ebola, Dengue fever, hemorrhagic shock, endotoxic shock, Rift valley fever, Marburg, Crimean-Congo hemorrhagic fever (CCHF), South American hemorrhagic fever, dengue, yellow fever, Omsk hemorrhagic fever virus, Kyasanur Forest, Junin, Machupo, Sabia, Guanarito, Garissa, Ilesha, or Lassa fever viruses.

In some embodiments, the disease or condition is vascular leakage, which may be caused by, for example, vascular leak syndrome, infectious disease, inflammatory diseases, inter alia, sepsis, lupus, irritable bowel disease, inflammatory bowel disease and inflammation of general vasculature.

In some embodiments, the disease or condition is selected from aging, chronic and acute inflammatory condition, chemically induced vascular inflammation, viral infection, bacterial infection, fungal infection, hypertension, coronary artery disease, heart failure, stroke, peripheral artery disease, myocardial infarction, diabetes, chronic renal failure, abnormal vascular smooth muscle cell proliferation, Type 2 diabetes, insulin resistance, Lupus, HIV, inflammation resulting from radiation and drug treatment, hemoglobinopathies, cytokine storm associated condition induced by viral disease, erectile dysfunction, leg ulcer, inflammation associated with increased populations of senescent cells occurring with age, sleep apnea, sepsis, and chronic obstructive pulmonary disease, cardiovascular disease, renal failure; hypertension, stroke and microemboli, open wound, sexual dysfunction, bladder dysfunction, neuropathic pain and cognitive decline.

In some embodiments, the disease or condition is selected from epilepsy treatment, anti-inflammatory, outcome of cbd treatment is associated with expectations, improved mood, anxiety treatment, potential in cancer treatment—reduced cell proliferation, breast cancer treatment, weight gain via adipogenesis, treatment of stress/stress reduction, cancer treatment, muscle pain—fibromyalgia, covid-19 treatment, stroke treatment, psychosis treatment, treatment of infection with staph a., treatment of depression, parkinson's disease treatment, bone fracture treatment, stroke treatment, diabetes treatment, epileptic seizure prevention, epilepsy treatment, alheizermers treatment, decrease in sperm count and motility, memory recovery from ptsd, anti-cancer agent, pain reduction, colon cancer, schizophrenia treatment. In some embodiments, the therapeutic agent comprises or consists of CBD.

In some embodiments, the disease or condition is selected from aged skin, reduce wrinkles, sores, sunburn and wound repair, eye disease (inflammation or dry eyes), pain or inflammation in bones or joints, osteoarthritis, acid reflux, interstitial cystitis, and bladder pain. In some embodiments, the therapeutic agent comprises or consists of hyaluronic acid.

The amount of the API included in the dosage form will generally depend upon the particular API or medicament, its intended use, and patient profile. The amount is generally selected in accordance with known principles of pharmacy. Effective amounts are generally that amount or quantity of an API, which is sufficient to elicit the required or desired therapeutic response (biological response) when administered to a patient. In some embodiments, the dosage form includes the API in amounts of up to about 1000 mg. In some embodiments, the dosage form includes the API/medicament(s) in amounts ranging from about 5 mg to about 150 mg. In some embodiments, the dosage form includes the API/medicament(s) in amounts of up to about 25 mg.

In some embodiments, there is provided a method of treating, ameliorating, mitigating, slowing, arresting, preventing or reversing age-associated obesity in a subject. In some embodiments, there is provided a method of treating, ameliorating, mitigating, slowing, arresting, preventing or reversing age-associated increases in blood lipid levels in a subject. In some embodiments, there is provided a method of treating, ameliorating, mitigating, slowing, arresting, preventing or reversing age-associated loss of insulin sensitivity in a subject. In some embodiments, there is provided a method of treating, ameliorating, mitigating, slowing, arresting, preventing or reversing age-associated impairment of memory function in a subject. In some embodiments, there is provided a method of treating, ameliorating, mitigating, slowing, arresting, preventing or reversing age-associated decline in eye function in a subject. In some embodiments, there is provided a method of treating, ameliorating, mitigating, slowing, arresting, preventing or reversing age-associated retinal degeneration in a subject. In some embodiments, there is provided a method of treating, ameliorating, mitigating, slowing, arresting, preventing or reversing dry eye. In some embodiments, there is provided a method of treating, ameliorating, mitigating, slowing, arresting, preventing or reversing age-associated dry eye.

These methods can each independently comprise, consist essentially of, or consist of administering to a subject a solid dosage form disclosed herein containing a therapeutically effective amount of a therapeutic agent (e.g. nicotinamide mononucleotide (NMN)). In some embodiments, the therapeutic agent (e.g. NMN) can be administered at a dosage rate of about 100 mg per day, from 100 mg per day to 2000 mg per day, or about 2000 mg per day. In some embodiments, the therapeutic agent (in the dosage form described herein) can be administered at a dosage rate of 0.5 mg, about 0.5 mg, 1 mg, about 1 mg, 5 mg, about 5 mg, 10 mg, about 10 mg, 20 mg, about 20 mg, 30 mg, about 30 mg, 40 mg, about 40 mg, 50 mg, about 50 mg, 60 mg, about 60 mg, 70 mg, about 70 mg, 80 mg, about 80 mg, 90 mg, about 90 mg, about 100 mg per day, 100 mg per day, 150 mg, about 150 mg, about 200 mg per day, 200 mg per day, about 300 mg per day, 300 mg per day, about 400 mg per day. 400 mg per day, about 500 mg per day, 500 mg per day, about 600 mg per day, 600 mg per day, about 700 mg per day, 700 mg per day, about 800 mg per day, 800 mg per day, about 900 mg per day, 900 mg per day, about 1000 mg per day, 1000 mg per day, about 1100 mg per day, 1100 mg per day, about 1200 mg per day, 1200 mg per day, about 1300 mg per day, 1300 mg per day, 1350 mg, about 1350 mg, about 1400 mg per day, 1400 mg per day, about 1500 mg per day, 1500 mg per day, about 1600 mg per day, 1600 mg per day, about 1700 mg per day, 1700 mg per day, about 1800 mg per day, 1800 mg per day, about 1900 mg per day, 1900 mg per day, about 2000 mg per day, 2000 mg per day, 2040 mg, about 2040 mg, 2250 mg, about 2250 mg, 2260 mg, about 2260 mg, 2700 mg, about 2700 mg, 2720 mg, about 2720 mg, 3400 mg, about 3400 mg, 3390 mg, about 3390 mg, 3400 mg, about 3400 mg, 3600 mg, about 3600 mg, 4080 mg, about 4080 mg, 4500 mg, about 4500 mg, 4520 mg, about 4520 mg, 5440 mg, about 5440 mg, 5650 mg, about 5650 mg, 6800 mg. about 6800 mg. or an alternation or combination thereof. In some embodiments. NMN can be administered at a dosage rate of about 100 mg/kg body weight/day, from 100 mg/kg body weight/day to 500 mg/kg body weight/day, or about 500 mg/kg body weight/day. In some embodiments, therapeutic agent can be administered at a dosage rate of about 100 mg/kg body weight/day, from 100 mg/kg body weight/day to 300 mg/kg body weight/day, or about 300 mg/kg body weight/day. In some embodiments, these methods can comprise, consist essentially of or consist of administering a solid dosage described herein once per day. In some embodiments, these methods can comprise, consist essentially of or consist of administering a solid dosage twice per day. The exact dosage may also vary depending on factors such as the age and disease condition of an individual and can be modified by a medical professional without undue experiments. The dosage form can also be administered once, twice, three times a day or as needed under the direction of a medical professional.

In some embodiments, there is provided a method of increasing NAD+ levels in a subject through administration of NMN in the dosage form described herein. In some embodiments, there is provided a method of treating age-associated defects in neural stem/progenitor cell (NSPC) functionality in a subject through administration of NMN. In some embodiments, there is provided a method of reducing age-associated decrease in a NSPC population in a subject through administration of NMN. In some embodiments, there is provided a method of maintaining at least one NSPC in a subject through administration of NMN. In some embodiments, there is provided a method of enhancing NAD biosynthesis in a subject through administration of NMN. In some embodiments, there is provided a method of promoting NSPC proliferation in a subject, in which the methods comprise administration of NMN to the subject. The methods of each of these embodiments can comprise, consist essentially of, or consist of administration of a therapeutically effective amount of NMN.

In some embodiments, there is provided a method of increasing bone density levels in a subject. In some embodiments, there is provided a method of treating aberrantly low bone density levels in a subject. In some embodiments, there is provided a method of treating an age-associated bone density decrease in a subject. In some embodiments, there is provided a method of treating osteoporosis in a subject. In some embodiments, there is provided a method of preventing an age-associated bone density decrease in a subject. The methods of each of these embodiments can comprise, consist essentially of, or consist of administration of a therapeutically effective amount of NMN.

In some embodiments, the dosage form disclosed herein is administered transmucosally to deliver a therapeutic agent to treat postpartum hemorrhage (PPH) in a non-invasive way. In some embodiments, the therapeutical agent is oxytocin. The agent can be administered sublingually or buccally.

In various embodiments, there is provided methods of preventing, methods of reducing risk of, and methods of treating various diseases associated with photoreceptor dysfunction, including, without limitation, age-related macular degeneration (AMD), inherited and acquired retinal diseases such as, without limitation, retinitis pigmentosa (RP), rod and cone dystrophism, and Leber's congenital amaurosis (LCA) by administration of NMN. In various embodiments, NMN administration can be an effective intervention for the prevention and/or treatment of orphan retinal degenerative diseases including but not limited to rod dystrophy, cone dystrophy, retinitis pigmentosa, other inherited retinal degenerations, Leber's congenital amaurosis (LCA) and acquired retinal degenerations such as, but not limited to, age-related macular degeneration photoreceptor degeneration following retinal detachment.

In some embodiments, there is provided a method of treating macular degeneration in a subject. In some embodiments, there is provided a method of treating aberrant retinal NAD levels in a subject, including aberrantly low retinal NAD levels. In some embodiments, there is provided a method of treating retinal degeneration in a subject. In some embodiments, there is provided a method of treating photoreceptor damage in a subject. In some embodiments, there is provided a method of treating photoreceptor degeneration in a subject. In some embodiments, there is provided a method of treating vision loss associated with retinal degeneration in a subject. In some embodiments, there is provided a method of treating vision loss in a subject. In some embodiments, there is provided a method of treating aberrant retinal structure in a subject. In some embodiments, there is provided a method of treating aberrant retinal function in a subject. In some embodiments, there is provided a method of treating aberrant retinal function in a subject. In some embodiments, there is provided a method of treating aberrant retinal function in a subject. In some embodiments, there is provided a method of increasing retinal NAD levels in a subject. In some embodiments, there is provided a method of reducing risk of developing macular degeneration in a subject. In some embodiments, there is provided a method of reducing risk of developing macular degeneration in a subject. In some embodiments, there is provided a method of reducing risk of developing aberrant retinal NAD levels in a subject. In some embodiments, there is provided a method of developing retinal degeneration in a subject. In some embodiments, there is provided a method of reducing risk of developing photoreceptor damage/degeneration in a subject. In some embodiments, there is provided a method of reducing risk of developing vision loss associated with retinal degeneration in a subject. In some embodiments, there is provided a method of reducing risk of developing vision loss in a subject. In some embodiments, there is provided a method of reducing risk of developing aberrant retinal structure in a subject. In some embodiments, there is provided a method of reducing risk of developing aberrant retinal structure in a subject. In some embodiments, there is provided a method of reducing risk of developing aberrant retinal function in a subject. In some embodiments, there is provided a method of developing aberrant retinal function in a subject. In some embodiments there is provided a method of treating a photoreceptor dysfunction in a subject. In some embodiments, there is provided a method of treating a retina disease in a subject. In various embodiments, these methods can comprise, consist essentially of, or consist of administering to a subject a pharmaceutically effective amount of nicotinamide mononucleotide (NMN). In some embodiments, a pharmaceutically effective amount of nicotinamide mononucleotide (NMN) can be an amount effective for increasing retinal NAD levels. In some embodiments a retina disease that can be treated by administration of NMN can be retinitis pigmentosa (RP), Leber's congenital amaurosis (LCA), rod dystrophy, cone dystrophy, rod-cone dystrophy, cone-rod dystrophy, age-related macular degeneration, photoreceptor degeneration following retinal detachments, or a combination thereof.

In some embodiments, the disease to be treated is selected from the group consisting of Parkinson's disease, erectile dysfunction, Alzheimer's disease, asthma, diarrhea, and migraine headache. The method can comprise, consist essentially of, or consist of administering to a subject a pharmaceutically effective amount of nicotinamide mononucleotide (NMN).

The dosage form can be placed in or near the sublingual mucosa or the buccal mucosa of the subject's mouth. In some embodiments, the dosage form contains polymers that provide mucoadhesive properties to the unit dosage form such as a film. The time period for which it is desired to maintain the film in contact with the mucosal tissue depends on the type of active contained in the dosage form. Generally, the buccal and/or sublingual delivery is capable of releasing the agents from within seconds to within hours and, more preferably, within at least about 60 minutes and, even more preferably, within about 40 minutes. In some embodiments, the dosage form for buccal and/or sublingual delivery should be dissolved within 5 to 20 minutes but be capable of delivering the agents over an extended period.

Some agents may only require a few minutes for delivery through the mucosal tissue, whereas other actives may require up to several hours or even longer. Accordingly, in some embodiments, one or more water-soluble polymers may be used to form the film. In other embodiments, however, it may be desirable to use combinations of water-soluble polymers and polymers that are water-swellable, water-insoluble and/or biodegradable. The inclusion of one or more polymers that are water-swellable, water-insoluble and/or biodegradable may provide films with slower dissolution or disintegration rates than films formed from water-soluble polymers alone. As such, the film may adhere to the mucosal tissue for longer periods or time, such as up to several hours, which may be desirable for delivery of certain active components.

In some embodiments, the method further includes administering a second agent selected from the group consisting of antihistamines, medications treat respiratory disorders, antiemetics, sleep aids, medications to treat diarrhea, oral hygiene agents, migraine treatments, CNS medicines, and first-aid medications.

The buccal and/or sublingual delivery of therapeutic agents are expected to reduce the severity of gastrointestinal side-effects of particular active compounds. Symptoms of gastrointestinal irritation include indigestion, pain, nausea, vomiting, cramps, hemorrhaging, kidney damage, liver damage, diarrhoea and flatulence.

This patent document further contemplates methods of treatment and/or prophylaxis of medical conditions in mammals and, in particular, humans by the administration of a dosage form which enhances the bioavailability of the therapeutic agent, its salts or its metabolic derivatives, pro-drugs, intermediates or complexes. The expression "in need of" includes a subject directly requiring the dosage form as well as situations where there is a perceived need to provide the treatment or where prophylaxis is required.

For example, there is a perceived need to develop a formulation having a prophylactic action to reduce the onset of Parkinson's disease. The Heart Research Institute is investigating using acetaminophen to inhibit the production of myeloperoxidase and the Harvard Medical School is investigating ibuprofen. Formulations according to the invention could be developed for these active compounds for use in these prophylactic treatments.

According to a further aspect of the patent document there is provided a method for reducing the amount of an agent necessary to achieve an effect in an individual as compared to a typical agent that is swallowed. The method comprises providing the buccal dosage forms described herein to an individual to achieve a specific effect. The buccal dosage form requires less than the typical amount of compound generally used in other formulations to achieve the effect. The buccal dosage form is placed in contact with the buccal membrane to thereby cause the compound to be released and absorbed optimally through the mucous membranes in a buccal cavity of the individual.

The dosage form described herein may be constructed in a manner known to those skilled in the art so as to give the predetermined controlled release of the compound. Typically, a formulation for a specific active compound will involve a multi step approach. By way of example, it may be that for a particular active compound, the issue of poor solubility (important for dissolution in the oral cavity) is addressed by pH adjustment or the addition of an enhancer or by altering the active compound by using its salt or some other derivative of the active compound. The same active compound might also exhibit poor membrane permeability and therefore require the addition of an enhancer to the formulation. It might also be possible to alter the structure of the active compound in different ways to facilitate its active transport across the buccal mucosa. Finally, the active compound, when released from the matrix, may exhibit an unacceptable taste. This would then require the inclusion of a suitable taste masking agent in the formulation. Where speed of onset is not considered a major factor, it may be viable to consider complexing the active compound, as an alternative to mask any taste, using a fatty acid or other compounds that may otherwise reduce membrane uptake of the bioactive compound or complex. A well known factor to one skilled in the art is that some complexation alternatives, while functioning effectively as taste maskers, also retard the uptake rate of the active.

A related aspect provides a method of delivering an API transmucosally to a subject. The method includes administering to the subject the dosage form disclosed herein. The scope and amount of the components/ingredients of the dosage form are as described above. In some embodiments, the components of the dosage form including one or more of the water soluble polymer, the surfactant, the softener, the fatty acid, other components described above, and their respective amounts are selected so that at least 3%, at least 4%, at least 5%, at least 6%, at least 7%, at least 8%, at least 9%, at least 10%, at least 11%, at least 12%, at least 15%, at least 18%, at least 20%, at least 25%, at least 30%, at least 35%, at least 40%, or at least 50% of the API in the dosage form is uptaken via oral transmucosal delivery. In some embodiments, the respective amounts of the surfactant and the fatty acid are selected so that the HLB of their combination ranges from about 8 to about 15, including for example, about 9, about 10, about 11, about 12, about 13, about 14 and about 15.

For example, the API uptake can be determined according to the following procedure:

(1) the test dosage form is placed under the tongue of the subject (no swallowing by subject) for 1 minute;

(2) rinse mouth with 20 ml water for 1 minute with swish water around the mouth for 30 times; collect all 20 ml mouth wash water; and (3) repeat rinsing process 2 more times (additional 60 ml water); and (4) detect the amount of the API (e.g. NMN) content in all the collected mouth wash water, and subtract this amount from the initial amount of API in the dosage form to get the uptake/absorption of the API via oral transmucosal delivery In any embodiments of the methods disclosed herein, the hold time of the dosage form placed under the tongue may vary depending on factors such as the loading of API and the specific components of the dosage form. In some embodiments, the hold time is about 1 minute, about 2 minutes, about 3 minutes, about 4 minutes, about 5 minutes or longer, or as needed.

Method of Manufacturing

Another aspect of the patent document provides a method of preparing the dosage form described herein. In some embodiments, the dosage form for buccal and/or sublingual delivery is manufactured using a dry manufacturing process with all the components blended in a normal dry powder process and compressed using a standard tabletting machine. Such dry formulations can be manufactured in commercial numbers and provided in conventional blister packaging. This process is applicable where the excipients are chosen to eliminate the need for any wet formulation or semi manual processing which are costly and time intensive.

In some embodiments, the method includes casting a mixture containing the API and the excipients onto a suitable film (e.g. Scotchpak PET film) or substrate (e.g. a mold), and allowing the mixture to dry and forming a coating. The drying step may be heated at for example a temperature ranging from about 25° C. to about 80° C. The coated film can then be cut into suitable size.

Tablets may be manufactured by well-known tableting procedures. In common tableting processes, materials to be tableted are deposited into a cavity, and one or more punch members are then advanced into the cavity and brought into intimate contact with the materials to be pressed, whereupon compressive force is applied. The materials are thus forced into conformity with the shape of the punches and the cavity. Hundreds, and even thousands, of tablets per minute can be produced in this fashion. Various tableting methods, well known to those skilled in the art, are comprehensively discussed in Lieberman, Pharmaceutical Dosage Form: Tablets, Vol. 1, 2nd Ed., pp 372-376, New York, 1989, which disclosure is incorporated herein by reference in its entirety.

Known granulation and wet-granulation methods for forming tablets may be utilized. Granulation generally includes any process of size enlargement whereby small particles are gathered together into larger, permanent aggregates to yield a free-flowing composition having a consistency suitable for tableting. Such granulated compositions may have consistency similar to that of dry sand. Granulation may be accomplished by agitation in mixing equipment or by compaction, extrusion or globulation. Granulation also includes, for example, a process where a liquid form of a material is rendered granular, or in a solid form, by combining it with a granular core material, such as a sugar particle. Such granular material may be produced, for example, by spray-drying the liquid onto the core particle. Thus, individual materials maybe granulated to lend themselves to tableting.

EXAMPLES

Example 1

The following table provides exemplary preparation of dosage forms. Conditions and agents may vary depend on factors including the specific agent, the intended use, the amount of excipients.

TABLE 1

| Manufacturing of Dosage Form<br>Methods of manufacturing: |
|---|
| Method #1 |
| 1. Cast coating mass on Scotchpak PET film, dry at 80 C. for 30 min or 40 C. for 4 hours.<br>2. Die-cut into 22 mm × 32 mm strips. |
| Method #2 |
| 1. Pour coating mass into a mold, dry at 80 C. for 30 min or 40 C. for 3 hours.<br>2. Cut the dry products into 22 mm × 32 mm strips. |
| Method #3 |
| 1. Weight accurately 380 mg of coating mass, evenly distribute it into a small sized mold of 22 mm × 32 mm.<br>2. Dry at 80 C. for 30 min or 40 C. for 3 hours.<br>3. Remove the dry product from the mold. |

TABLE 2

Exemplary API and excipients

| Ingredients | Examples | Weight Range | Functions |
|---|---|---|---|
| API | NMN, caffeine, curcumine, PAC, Astaxanthin, Resveratrol, etc | 5%-80% | Active ingredients |
| Water soluble polymers | PVP, PU, HPMC, PEO, PVA, CMC-Na, Polyacrylate | 5%-50% | Film Forming |
| High viscous polymers | Xanthan Gum, HPMC, Konjac gum, HMW CMC-Na | 0.25%-5% | Thickener or Taste Masking |
| Absorption Enhancers | Oleic Acid, Labrafil M1944 CS | 0.25%-5% | Absorption enhancers |
| Surfactant | Tween 80, | 0.25%-10% | Surfactant |
| Softener | Glycerin, Propylene glycol, PEG400 | 2%-15% | Plasticizer |
| Binder | Sorbitol, NMN | 1%-50% | Binder |
| Sweetener | Sucrose, Sucralose, aspartame | 0.1%-5% | Taste Masking |
| Stabilizer | EDTA | 0.1%-5% | Stabilizer |
| Others | FD&C colors, BHA & BHT, flavoring agents | 0.1%-5% | Flavor and color agents, Anti-oxidants |

Example 2

TABLE 3

NMN Oral Thin Film Formulations

| | NMN OTF Formulation | | | | | |
|---|---|---|---|---|---|---|
| | Formula #N1 | Formula #N2 | Formula #N3 | Formula #N4 | Formula #N5 | Formula #N6 |
| API (Beta-nicotinamide mononucleotide) | 75.00% | 75.00% | 75.00% | 75.00% | 75.00% | 75.00% |
| HPMC | 2.00% | | | | | |
| PEO | 9.47% | | | | | |
| PU | 6.00% | | | 11.72% | | |
| PVA | | 1.97% | 9.22% | | | 5.47% |
| PVP | | | | | 11.22% | 6.00% |
| CMC Na | | | | 0.75% | | 0.75% |
| Konjac Gum | 0.75% | | 0.50% | | | |
| Oleic Acid | 0.50% | | | 1.40% | 1.00% | 1.00% |
| Tween 80 | 6.50% | 4.25% | | 2.60% | | 3.50% |
| Labrafil M1944 CS | | 2.00% | 4.50% | | 4.00% | |
| Glycerin (Propylene Glycol, or PEG400) | 5.00% | 10.00% | 10.00% | 7.00% | 8.00% | 7.50% |
| Menthol | 0.18% | 0.18% | 0.18% | 0.18% | 0.18% | 0.18% |
| EDTA | 0.18% | 0.18% | 0.18% | 0.18% | 0.18% | 0.18% |
| Sucralose | 0.40% | 0.40% | 0.40% | 0.40% | 0.40% | 0.40% |
| FD&C Blue #1 | 0.03% | 0.03% | 0.03% | 0.03% | 0.03% | 0.03% |
| SUM | 100.00% | 100.00% | 100.00% | 99.25% | 100.00% | 100.00% |

Example 3

TABLE 4

| Combinational NMN Oral Thin Film Formulations | | | | | | | |
|---|---|---|---|---|---|---|---|
| | Formulation | | | | | | |
| | Formula #C1 | Formula #C2 | Formula #C3 | Formula #C4 | Formula #C5 | Formula #C6 | Formula #C7 |
| NMN | 70.00% | 70.00% | 70.00% | 70.00% | 70.00% | 70.00% | 70.00% |
| Caffeine | 5.00% | | | 5.00% | 5.00% | 5.00% | |
| Curcumin | 1.00% | | 5.00% | 1.00% | | | 5.00% |
| proanthocyanidins (PAC) | | 5.00% | | | 5.00% | 2.00% | |
| HPMC | 2.00% | | | | | | |
| PEO | 10.97% | | | | | | |
| PU | | 6.00% | | 11.47% | | 10.50% | |
| PVA | | 3.75% | 9.25% | | | | 5.50% |
| PVP | | | | | 6.25% | | 6.00% |
| CMC Na | | | | 0.75% | | 0.75% | 0.75% |
| Konjac Gum | 0.75% | | 0.50% | | | | |
| Oleic Acid | | 0.25% | 0.50% | 1.40% | | 1.40% | 1.00% |
| Tween 80 | | 4.25% | 4.00% | 2.60% | | 2.60% | |
| Labrafil M1944 CS | 4.50% | | | | 5.00% | | 3.50% |
| Glycerin | 5.00% | 10.00% | 10.00% | 7.00% | 8.00% | 7.00% | 7.50% |
| Menthol | 0.18% | 0.18% | 0.18% | 0.18% | 0.18% | 0.18% | 0.18% |
| EDTA | 0.18% | 0.18% | 0.18% | 0.18% | 0.18% | 0.18% | 0.18% |
| Sucralose | 0.40% | 0.40% | 0.40% | 0.40% | 0.40% | 0.40% | 0.40% |
| FD&C Blue #1 | 0.03% | | | 0.03% | | | |
| SUM | 100.00% | 100.00% | 100.00% | 100.00% | 100.00% | 100.00% | 100.00% |

Example 4

TABLE 5

| HLB value estimates of a solution combining oleic acid and Tween 80. | | | | | | | | | | | |
|---|---|---|---|---|---|---|---|---|---|---|---|
| OA/Tw80 | HLB | S1 | S2 | S3 | S4 | S5 | S6 | S7 | S8 | S9 | S10 |
| Oleic Acid | 1 | 5% | 10% | 20% | 30% | 40% | 50% | 60% | 70% | 80% | 90% |
| TWEEN80 (polysorbate 80) | 15 | 95% | 90% | 80% | 70% | 60% | 50% | 40% | 30% | 20% | 10% |
| (Final HLB) | | 14.3 | 13.6 | 12.2 | 10.8 | 9.4 | 8 | 6.6 | 5.2 | 3.8 | 2.4 |

A HLB value between 7-14 is associated with suitable film dosage appearance and desirable API permeation. The HLB value can be estimated by the equation below:

$$HLB=7+\Sigma H_{h,i}-\Sigma H_{l,i}$$

Where $H_{h,i}$ represents the value of hydrophilic group and HI, represents the value of the lipophilic group numbers. Values of common chemical groups are well known in the literature, including Shinoda, et al., Emulsions and Solubilization, John Wiley and Sons, New York (1986); Nollet, et al., International Journal of Cosmetic Science, 2019, 41, 99-108; Davis, Colloids Surf. A. 1994, 91, 9. The entire disclosure of these references are hereby incorporated by reference.

TABLE 5.1

| Selected HLB Group Numbers | | | |
|---|---|---|---|
| Hydrophilic Group | Group Number | Lipophilic Group | Group Number |
| $—SO_4NA^+$ | 38.7 | —CH— | 0.475 |
| $—COOH^+$ | 21.2 | $—CH_2—$ | 0.475 |
| Tetiary amine | 9.4 | $—CH_3—$ | 0.475 |
| Sorbitan ring | 6.8 | | |
| —COOH | 2.1 | | |
| —O— | 1.3 | | |

The HLB value of a mixture of two components (weight concentrations of x and y, HLB values of HLB1 and HLB2, respectively) can be estimated as HLB value of mixture=x*HLB1+y*HLB2.

Example 5

TABLE 6

| Caffeine Oral Thin Film Formulation | | |
|---|---|---|
| | Caffeine Formulation | |
| | CF1 Dry (%) | CF2 Dry (%) |
| Caffeine | 50.0% | 40.0% |
| NMN | 0.0% | 10.0% |
| Pullulan | 33.50% | 33.5% |
| Methocel K100M | 1.00% | 1.0% |
| QA/TW80 (35:65) | 5.00% | 5.0% |
| Glycerin | 8.0% | 8.0% |
| Sucralose | 1.50% | 1.5% |
| Sorbitol | 1.00% | 1.0% |
| SUM | 100.00% | 100.0% |

Preparation of Formulation CF1 (Refer to Table 6) results in a prototype with poor product characteristics such as brittleness. An addition of 10% NMN content of Formulation CF2 will improve the product property significantly. NMN can act as a binder in the caffeine oral formulation.

Example 6

TABLE 7

| Film dosage form for caffeine | | | | | | | | | | |
|---|---|---|---|---|---|---|---|---|---|---|
| | Formula Code | | | | | | | | | |
| | FLA# 5A | FLA# 5B | FLA# 5C | FLA# 5D | FLA# 5E | FLA# 5F | FLA# 5G | FLA# 5H | FLA# 5I | FLA# 5J |
| Caffeine | 20.0% | 20.0% | 20.0% | 20.0% | 20.0% | 20.0% | 20.0% | 20.0% | 20.0% | 20.0% |
| Pullulan | 66.0% | 79.0% | 71.0% | 70.5% | 67.0% | 77.0% | 78.0% | 77.0% | 78.7% | 77.0% |
| Methocel K100M | 0.3% | 0.25% | 0.3% | 0.3% | 0.3% | 0.3% | 0.3% | 0.3% | 0.3% | 0.3% |
| Glycerin | 8.0% | | 8.0% | 8.0% | 8.0% | | | | | |
| Oleic Acid | 1.0% | | | 0.25% | 1.0% | 1.0% | 1.0% | 2.0% | | |
| Tween 80 | 4.0% | | | 0.25% | 3.0% | 1.0% | | | 0.25% | 2.0% |
| Menthol | 0.2% | 0.2% | 0.2% | 0.2% | 0.2% | 0.2% | 0.2% | 0.2% | 0.2% | 0.2% |
| EDTA | 0.2% | 0.2% | 0.2% | 0.2% | 0.2% | 0.2% | 0.2% | 0.2% | 0.2% | 0.2% |
| Sucralose | 0.4% | 0.4% | 0.4% | 0.4% | 0.4% | 0.4% | 0.4% | 0.4% | 0.4% | 0.4% |
| SUM | 100.0% | 100% | 100% | 100% | 100% | 100% | 100% | 100% | 100% | 100% |
| Variables | Average concentration | | No OA/Tw80 | Low OA/Tw80 | OA/TW80 (4%) | No Glycerin | No Tw80 | No Tw80 | Low Tw80 | 2% Tw80 |
| Resulting film physical observations | Good film | Surfaces shrinkage on edges | shrinkage on edges | Shrinkage observed | Perfect coating. | Good spreading | Not good spreading | Not good spreading | Improve spreading, but not good enough | Good Spreading |

General procedures for manufacturing oral thin films: a coating solution was prepared by adding aqueous water solution into a homogeneous mixture of ingredients (see for example Table 3&4). The resulting mixture contained a solid content of approximately 20-8000 depending on the viscosity of the mixture. The coating mixture mass was degassed in a vacuum mixer, coated on a polyester film, and dried in a hot air circulating oven at 25-100° C. to form a thin film. The film was then cut into dosage units ready for packaging.

Example 7

Three dosage forms for Oxytocin (OXYA, OXYB and OXYC) were prepared as shown in Table 8. The weight of the components of the dosage form are measured in mg.

TABLE 8

| Dosage forms for Oxytocin | | | |
|---|---|---|---|
| Formulation | OXYA | OXYB | OXYC (no-enhancers) |
| Oxytocin | 5.00 | 5.00 | 5.00 |
| Pullulan | 13.50 | 10.99 | 18.00 |
| Tween80 | 3.00 | 3.00 | no |
| Oleic Acid | 1.50 | 1.50 | no |
| Glycerin | 2.00 | 2.00 | 2.00 |
| Citric Acid | no | 2.50 | no |
| FD&C Blue#1 | 0.01 | 0.01 | 0.01 |
| SUM | 25.00 | 25.00 | 25.01 |

In-vitro Permeation testing was performed for the dosage forms in Table 8 with a Franz Cell Diffusion System. The receiving chamber was filled in water solution and stirred with magnetic bar. Fix the PermeaPad® Barrier membrane at the surface. The PermeaPad® Barrier consists of two cellulose membranes and in between there is a Lipid layer Lecithine (S-100). Place the donating chamber onto the receiving chamber and effectively sandwich the membrane. Add 5 mg of the film prepared in Table 8 into the donating chamber and introduce 1 ml of water to dissolve the film. Start the timer for the experiment.

Permeability (P, cm/h), in general within first 8 hours, is defined as the rate of flow of liquid through the membrane. It is calculated by:

$$P = \frac{\Delta C_{receptor}}{\Delta t * A_{CrossSection}} \cdot \frac{V_{receptor}}{C_{donor}}$$

TABLE 9

Permeability (cm/h) of hydrophilic drug molecules with a MW ranging from 100 to 6000 g/mol through PermeaPad biomimetric membrane using a Franz Cell diffusion system in vitro.

| Active | Molecular weight (MW, g/mol) | Pemeability (cm/h) via PermeaPad Biomimetic Membrane in vitro |
|---|---|---|
| Caffeine | 194.19 | 0.277 (no enhancers), 5.01 (HLB15), 7.76 (HLB9.4) |
| Apomorphine HCL | 312.71 | 0.413 (no enhancers), 1.87 (HLB15), 2.73 (HLB9.0) |
| Beta-nicotinamide mononucleotide, NMN | 334.2 | 0.23 (No enhancers), 0.23 (HLB4.3), 0.38 (HLB9.4) |
| Montelukast Na | 608.17 | 0.17 (no enhancers), 0.57 (HLB4.3), 0.65 (HLB9.0) |
| Oxytocin Peptide | 1007.19 | 0.028 (OXYC-No enhancers), 0.055 (OXYA-HLB10.3), 0.048 (OXYB-HLB10.3) |

TABLE 9-continued

Permeability (cm/h) of hydrophilic drug molecules with a MW ranging from 100 to 6000 g/mol through PermeaPad biomimetric membrane using a Franz Cell diffusion system in vitro.

| Active | Molecular weight (MW, g/mol) | Pemeability (cm/h) via PermeaPad Biomimetic Membrane in vitro |
|---|---|---|
| Bivalirudin Peptide | 2180 | Un-detectable |
| Insulin | 5808 | Un-detectable |

The permeability of oxytocin (a small peptide with Molecular weight of 1007 g/mol) from the three dosage forms was tested through PermeaPad biomimetric membrane using a Franz Cell diffusion system in vitro. Formulations OXYA (HLB=10.3) and OXYB (HLB=10.3) provide more than 50% permeability in comparison to OXYC (no fatty acid and surfactant as enhancers).

The similar procedure was performed for the other APIs with a molecule weight ranging from 100 to 6000 g/mol. The permeability was calculated in Table 9.

Example 8

Oral thin film dosage forms for delivery of CBD were prepared. The ODF delivery system rapidly disintegrates and dissolves to release the CBD for oral mucosal and intragastric absorption and as a result can provide fast onset and fast pain relief.

TABLE 10

Formulations of CBD

| | CBD OTF Formulation | | | | | |
|---|---|---|---|---|---|---|
| | Formula #N1 | Formula #N2 | Formula #N3 | Formula #N4 | Formula #N5 | Formula #N6 |
| CBD Cannabidiol | 30.00% | 30.00% | 30.00% | 30.00% | 30.00% | 30.00% |
| HPMC | 2.00% | | | | | |
| PEO | 38.47% | | | | | |
| PU | | 6.00% | | 45.5% | | |
| PVA | | 36.22% | 58.72% | | | 39.97% |
| PVP | | | | | 43.72% | 6.00% |
| CMC Na | | | | 0.75% | | 0.75% |
| Konjac Gum | 0.75% | | 0.50% | | | |
| Oleic Acid | 10.00% | 5.00% | | 5.00% | 7.50% | 5.00% |
| Tween 80 | 12.00% | 12.00% | | 10.00% | 10.00% | 10.00% |
| Glycerin | 5.00% | 10.00% | 10.00% | 7.00% | 8.00% | 7.50% |
| Menthol | 0.18% | 0.18% | 0.18% | 0.18% | 0.18% | 0.18% |
| EDTA | 0.18% | 0.18% | 0.18% | 0.18% | 0.18% | 0.18% |
| Sucralose | 0.40% | 0.40% | 0.40% | 0.40% | 0.40% | 0.40% |
| TiO2 | 1.00% | | | 1.00% | | |
| FD&C Blue #1 | 0.03% | 0.03% | 0.03% | 0.03% | 0.03% | 0.03% |
| SUM | 100.00% | 100.00% | 100.00% | 100.00% | 100.00% | 100.00% |

TABLE 11

Formulations of THC

| | Formulation | | | | | |
|---|---|---|---|---|---|---|
| | Formula #N1 | Formula #N2 | Formula #N3 | Formula #N4 | Formula #N5 | Formula #N6 |
| THC (tetrahydrocannabinol) | 30.00% | 30.00% | 30.00% | 30.00% | 30.00% | 30.00% |
| HPMC | 2.00% | | | | | |
| PEO | 38.47% | | | | | |
| PU | | 6.00% | | 45.47% | | |
| PVA | | 36.22% | 58.72% | | | 39.97% |
| PVP | | | | | 43.72% | 6.00% |
| CMC Na | | | | 0.75% | | 0.75% |

TABLE 11-continued

| Formulations of THC | | | | | | |
|---|---|---|---|---|---|---|
| | Formulation | | | | | |
| | Formula #N1 | Formula #N2 | Formula #N3 | Formula #N4 | Formula #N5 | Formula #N6 |
| Konjac Gum | 0.75% | | 0.50% | | | |
| Oleic Acid | 10.00% | 5.00% | | 5.00% | 7.50% | 5.00% |
| Tween 80 | 12.00% | 12.00% | | 10.00% | 10.00% | 10.00% |
| Glycerin | 5.00% | 10.00% | 10.00% | 7.00% | 8.00% | 7.50% |
| Menthol | 0.18% | 0.18% | 0.18% | 0.18% | 0.18% | 0.18% |
| EDTA | 0.18% | 0.18% | 0.18% | 0.18% | 0.18% | 0.18% |
| Sucralose | 0.40% | 0.40% | 0.40% | 0.40% | 0.40% | 0.40% |
| TiO2 | 1.00% | | | 1.00% | | |
| Colorants | 0.03% | 0.03% | 0.03% | 0.03% | 0.03% | 0.03% |
| SUM | 100.00% | 100.00% | 100.00% | 100.00% | 100.00% | 100.00% |

TABLE 12

| Formulations of hyaluronic acid | | | | | | |
|---|---|---|---|---|---|---|
| | Formulation | | | | | |
| | Formula #N1 | Formula #N2 | Formula #N3 | Formula #N4 | Formula #N5 | Formula #N6 |
| Hyaluronic acid (HA) | 30.00% | 30.00% | 30.00% | 30.00% | 30.00% | 30.00% |
| HPMC | 2.00% | | | | | |
| PEO | 38.47% | | | | | |
| PU | | 6.00% | | 45.47% | | |
| PVA | | 36.22% | 58.72% | | | 39.97% |
| PVP | | | | | 43.72% | 6.00% |
| CMC Na | | | | 0.75% | | 0.75% |
| Konjac Gum | 0.75% | | 0.50% | | | |
| Oleic Acid | 10.00% | 5.00% | | 5.00% | 7.50% | 5.00% |
| Tween 80 | 12.00% | 12.00% | | 10.00% | 10.00% | 10.00% |
| Glycerin | 5.00% | 10.00% | 10.00% | 7.00% | 8.00% | 7.50% |
| Menthol | 0.18% | 0.18% | 0.18% | 0.18% | 0.18% | 0.18% |
| EDTA | 0.18% | 0.18% | 0.18% | 0.18% | 0.18% | 0.18% |
| Sucralose | 0.40% | 0.40% | 0.40% | 0.40% | 0.40% | 0.40% |
| TiO2 | 1.00% | | | 1.00% | | |
| Colorants | 0.03% | 0.03% | 0.03% | 0.03% | 0.03% | 0.03% |
| SUM | 100.00% | 100.00% | 100.00% | 100.00% | 100.00% | 100.00% |

TABLE 13

| Formulations of hyaluronic acid | | | | | | |
|---|---|---|---|---|---|---|
| | Formulation | | | | | |
| | Formula #N1 | Formula #N2 | Formula #N3 | Formula #N4 | Formula #N5 | Formula #N6 |
| Hyaluronic acid (HA) | 50.00% | 50.00% | 50.00% | 50.00% | 50.00% | 50.00% |
| HPMC | 2.00% | | | | | |
| PEO | 18.47% | | | | | |
| PU | | 6.00% | | 25.5% | | |
| PVA | | 16.22% | 38.72% | | | 19.97% |
| PVP | | | | | 23.72% | 6.00% |
| CMC Na | | | | 0.75% | | 0.75% |
| Konjac Gum | 0.75% | | 0.50% | | | |
| Oleic Acid | 10.00% | 5.00% | | 5.00% | 7.50% | 5.00% |
| Tween 80 | 12.00% | 12.00% | | 10.00% | 10.00% | 10.00% |
| Glycerin | 5.00% | 10.00% | 10.00% | 7.00% | 8.00% | 7.50% |
| Menthol | 0.18% | 0.18% | 0.18% | 0.18% | 0.18% | 0.18% |

TABLE 13-continued

| Formulations of hyaluronic acid | | | | | | |
|---|---|---|---|---|---|---|
| | Formulation | | | | | |
| | Formula #N1 | Formula #N2 | Formula #N3 | Formula #N4 | Formula #N5 | Formula #N6 |
| EDTA | 0.18% | 0.18% | 0.18% | 0.18% | 0.18% | 0.18% |
| Sucralose | 0.40% | 0.40% | 0.40% | 0.40% | 0.40% | 0.40% |
| TiO2 | 1.00% | | | 1.00% | | |
| Colorants | 0.03% | 0.03% | 0.03% | 0.03% | 0.03% | 0.03% |
| SUM | 100% | 100% | 100% | 100% | 100% | 100% |

TABLE 14

| Formulations of hyaluronic acid and CBD or THC | | | | | | |
|---|---|---|---|---|---|---|
| | Formulation | | | | | |
| | Formula #N1 | Formula #N2 | Formula #N3 | Formula #N4 | Formula #N5 | Formula #N6 |
| Hyaluronic acid (HA) | 41.67% | 41.67% | 41.67% | 41.67% | 41.67% | 41.67% |
| CBD or THC | 8.33% | 8.33% | 8.33% | 8.33% | 8.33% | 8.33% |
| HPMC | 2.00% | | | | | |
| PEO | 18.47% | | | | | |
| PU | | 6.00% | | 25.5% | | |
| PVA | | 16.22% | 38.72% | | | 19.97% |
| PVP | | | | | 23.7% | 6.00% |
| CMC Na | | | | 0.75% | | 0.75% |
| Konjac Gum | 0.75% | | 0.50% | | | |
| Oleic Acid | 10.00% | 5.00% | | 5.00% | 7.50% | 5.00% |
| Tween 80 | 12.00% | 12.00% | | 10.00% | 10.00% | 10.00% |
| Glycerin | 5.00% | 10.00% | 10.00% | 7.00% | 8.00% | 7.50% |
| Menthol | 0.18% | 0.18% | 0.18% | 0.18% | 0.18% | 0.18% |
| EDTA | 0.18% | 0.18% | 0.18% | 0.18% | 0.18% | 0.18% |
| Sucralose | 0.40% | 0.40% | 0.40% | 0.40% | 0.40% | 0.40% |
| TiO2 | 1.00% | | | 1.00% | | |
| Colorants | 0.03% | 0.03% | 0.03% | 0.03% | 0.03% | 0.03% |
| SUM | 100% | 100% | 100% | 100% | 100% | 100% |

Example 9

The impact of the different combinations of components on uptake or absorption of the API via oral transmucosal delivery was examined. As shown in Table 14, the transmucosal uptake of NMN through sublingual mucosa and/or buccal mucosa varies depending on the amounts of the dosage components including fatty acid and surfactant.

The general procedure for determining the API uptake is as follows:

(1) the test dosage form is placed sublingually under the tongue of the subject (no swallowing by subject) for 1 minute;

(2) rinse mouth with 20 ml water for 1 minute with swish water around the mouth for 30 times; collect all 20 ml mouth wash water;

(3) repeat rinsing process 2 more times (additional 40 ml water);

(4) detect the amount of the API (e.g. NMN) content in all the collected mouth wash water, and subtract this amount from the initial amount of API in the dosage form to get the uptake/absorption of the API via oral transmucosal delivery

TABLE 15

| Dosage forms of NMN and transmucosal uptake | | | | | | |
|---|---|---|---|---|---|---|
| | N1 % | N2 % | N3 % | N4 % | N5 % | N6 % |
| NMN | 70 | 70 | 70 | 70 | 70 | 70 |
| pullulan | 30 | 16 | 16 | 16 | 16 | 16 |

TABLE 15-continued

Dosage forms of NMN and transmucosal uptake

| | N1 % | N2 % | N3 % | N4 % | N5 % | N6 % |
|---|---|---|---|---|---|---|
| Glycerin | 0 | 14 | 7 | 0 | | 4 |
| Oleic acid | 0 | 0 | 0 | 14 | 10 | 4 |
| Tween 80 | 0 | 0 | 7 | 0 | 4 | 6 |
| | 100 | 100 | 100 | 100 | 100 | 100 |
| HLB | NA | NA | HLB = 15 | HLB = 1 | HLB = 5.0 | HLB = 9.4 |
| % uptake | 2.83% | 4.84% | 9.04% | 4.45% | 7.73% | 17.10% |

It will be appreciated by persons skilled in the art that invention described herein are not limited to what has been particularly shown and described. Rather, the scope of the invention is defined by the claims which follow. It should further be understood that the above description is only representative of illustrative examples of embodiments. The description has not attempted to exhaustively enumerate all possible variations. The alternate embodiments may not have been presented for a specific component of the dosage form or a step of the method, and may result from a different combination of described excipient or agent, or that other un-described alternate embodiments may be available for a dosage form or method, is not to be considered a disclaimer of those alternate embodiments. It will be appreciated that many of those un-described embodiments are within the literal scope of the following claims, and others are equivalent.

The invention claimed is:

1. A solid dosage form for oral transmucosal delivery of an active pharmaceutical ingredient (API), comprising a therapeutically effective amount of API for oral transmucosal delivery;

a water soluble polymer in an amount less than 50% of the dosage form by weight, a surfactant, a softener, and a fatty acid;

wherein the surfactant ranges from about 1% to about 10% in the dosage form, and wherein the respective amounts of the surfactant and the fatty acid are selected so that the HLB of their combination ranges from about 8 to about 13, wherein the dosage form is a film.

2. The dosage form of claim 1, which the API comprises an agent selected from the group consisting of nicotinamide mononucleotide (NMN), caffeine, curcumin, proanthocyanidins (PAC), astaxanthin, resveratrol, allicin, melatonin, cysteine, vitamin C, biotin, and any combination thereof.

3. The dosage form of claim 1, which the API comprises at least 10% by weight NMN and optionally one or more ingredients selected from the group consisting of caffeine, curcumin, proanthocyanidins (PAC), astaxanthin, resveratrol, allicin, melatonin, cysteine, vitamin C, and biotin.

4. The dosage form of claim 1, wherein the API is NMN.

5. The dosage form of claim 1, which the API is a peptide having a molecular weight of 1200 daltons or less.

6. The dosage form of claim 1, wherein the fatty acid ranges from about 0.2% to about 6% by weight in the dosage form.

7. The dosage form of claim 1, wherein the surfactant is selected from the group consisting of polyoxyethylene (20), sorbitan monooleate (polysorbate 80), and any combination thereof.

8. The dosage form of claim 1, wherein the fatty acid is present, and the ratio between the fatty acid and the surfactant ranges from about 1:1 to about 1:8 by weight.

9. The dosage form of claim 1, wherein the surfactant is polysorbate 80, and the fatty acid is oleic acid.

10. The dosage form of claim 9, wherein the respective amounts of the polysorbate 80 and the oleic acid are selected so that the HLB of their combination ranges from about 9 to about 12.

11. The dosage form of claim 9, wherein the ratio between the oleic acid and the surfactant ranges from about 1:1.5 to about 1:5 by weight, and their weight together ranges from about 3% to about 15% by weight in the dosage form.

12. The dosage form of claim 9, wherein the surfactant ranges from about 2.5% to about 6.5% by weight in the dosage form.

13. The dosage form of claim 1, wherein the water soluble polymer is selected from the group consisting of polyvinylpyrrolidone (PVP), pullulan (PU), (hydroxypropyl methylcellulose (HPMC), polyethyl oxide (PEO), polyvinyl alcohol (PVA), sodium carboxymethyl cellulose (CMC-Na), sodium alginate, Konjac gum, carigena, polyacrylates, polymethacrylates, copolymers thereof, and any combination thereof, wherein the polymer is less than 15% by weight in the dosage form.

14. The dosage form of claim 11, wherein the water soluble polymer, the surfactant, and their respective amounts are selected so that the dosage form is capable of loading the API in an amount of at least 50% by weight in the dosage form.

15. The dosage form of claim 1, wherein the softener ranges from about 5% to about 15% by weight in the dosage form, wherein the softener is selected from the group consisting of glycerin, propylene glycol, butylene glycol, and polyethylene glycol.

16. The dosage form of claim 1, wherein the API is in the dosage form by more than 50% by weight.

17. A method of treating a disease or condition in a subject, comprising administering transmucosally to the subject a dosage form of claim 1.

18. The method of claim 17, wherein the disease is selected from the group consisting of neurodegenerative diseases, muscular dystrophy, metabolic disease, and cardiovascular diseases.

19. The method of claim 17, wherein the disease is selected from the group consisting of Alzheimer's disease, multiple sclerosis, Parkinson's disease, amyotrophic lateral sclerosis, cerebral ischemic disease, Huntington's disease, spinal muscular atrophy, stroke, brain trauma, spinal cord injury, prion disease and diabetic neuropathy.

20. The method of claim 17, wherein the disease is selected from the group consisting of arrhythmia, ischemic heart disease, hypertensive heart disease and pulmonary hypertensive heart disease, valvular disease, and congenital heart disease, Alzheimer's disease, multiple sclerosis, Parkinson's disease, amyotrophic lateral sclerosis, cerebral ischemic disease, Huntington's disease, spinal muscular atrophy, stroke, brain trauma, spinal cord injury, prion disease, diabetic neuropathy, attention deficient disorder, attention deficient hyperactivity disorder (ADHD), learning disorders, neurocognitive disorders, Tic disorders, autism spectrum disorder, Tourette's disorder, schizophrenia, negative symptoms of schizophrenia, cognitive symptoms of schizophrenia, substance/medication-induced psychotic disorder, psychotic disorder due to another medical condition, brief psychotic disorder, schizophreniform disorder, schizoaffective disorder, disruptive mood dysregulation disorder, depression, post-partum depression, post-partum hemorrhage (PPH), persistant depressive disorder (dysthymia), major depressive episode, major depressive disorder, treatment-resistant depression, post-traumatic stress disorder, reactive attachment disorder, disinhibited social engagement disorder, personality disorders, psychopathy, cyclothymic disorder, manic episode, hypomanic episode, bipolar disorder, delusional disorder, obsessive compulsive disorder, hoarding disorder, premenstrual dysphoric disorder, somatic symptom, intellectual disabilities, communication disorders, motor disorders, catalepsy, catatonia, agitation, hypertension, sleep disorders, sexual dysfunctions, anxiety disorders, adjustment disorders, body dysmorphic disorder, Trichotillomania, excoriation disorder, substance/medication-induced obsessive-compulsive disorder, dementias, cognitive impairment, Alzheimer's disease, lewy body dementia, frontotemporal dementia, traumatic brain injury, prion diseases, Huntingtion's disease, Parkinson's disease, chronic traumatic encephalopathy, amyotrophic lateral sclerosis, mixed dementias, vascular dementia, hydrocephalus, seasonal affective disorder, pseudobulbar affect, cluster headache, headaches, migraines, Tension-type headaches, tinnitus, hallucinations, delusions, epilepsies, cyclic vomiting syndrome, cannabinoid hyperemesis, nausea, restless leg syndrome, weight loss or binge eating, anorexia nervosa, bulimia nervosa, alcoholism, nicotine dependence, substance use disorders, non-substance related disorders, oppositional defiant disorder, intermittent explosive disorder, conduct disorder, pyromania, kleptomania, paraphilic disorders, medication induced movement disorders, adverse effects of other medications, autoimmune diseases, acute pain, chronic pain, neuropathic pain, cancer, cough, infections, tinnitus, hearing loss, loss of taste, loss of smell, endocrine diseases and disorders, diabetes, gastrointestinal tract related diseases, urinary tract diseases, blood diseases, cardiovascular disease, inflammatory diseases, arthritis, paralysis, spinal cord injury, coagulation, seizure, inflammation, weight gain via adipogenesis, anxiety, abnormal cell proliferation, stress, muscle pain, covid-19, long covid, stroke, psychosis, infection with staph A, depression, diabetes mellitus (type 1 and type 2), postpartum bleeding or hemorrhage, acromegaly/carcinoid syndrome, auto-immune and immunodeficiency disorders, and chronic kidney disease-associated pruritus (CKD-aP).

* * * * *